US008821419B1

(12) United States Patent
Van Beek

(10) Patent No.: US 8,821,419 B1
(45) Date of Patent: Sep. 2, 2014

(54) FLEXIBLE INTERFACE EXTERNAL MICRO VACUUM CHAMBER TISSUE EXPANDER

(76) Inventor: Allen L. Van Beek, Edina, MN (US)

( * ) Notice: Subject to any disclaimer, the term of this patent is extended or adjusted under 35 U.S.C. 154(b) by 163 days.

(21) Appl. No.: 13/134,060

(22) Filed: May 27, 2011

(51) Int. Cl.
*A61H 7/00* (2006.01)
(52) U.S. Cl.
USPC .......................................................... 601/6
(58) Field of Classification Search
USPC .................. 601/6–14; 604/313, 315, 316
See application file for complete search history.

(56) References Cited

U.S. PATENT DOCUMENTS

| 387,904 | A | * | 8/1888 | Parker | 601/11 |
| 1,863,534 | A | * | 6/1932 | Odell | 601/11 |
| 1,936,129 | A | * | 11/1933 | Fisk | 604/313 |
| 3,382,867 | A | * | 5/1968 | Reaves | 601/7 |
| 5,000,164 | A | * | 3/1991 | Cooper | 601/11 |
| 5,577,994 | A | * | 11/1996 | Celik | 601/6 |
| 5,938,626 | A | * | 8/1999 | Sugerman | 601/6 |
| 6,468,235 | B2 | * | 10/2002 | Ito et al. | 601/6 |
| 2005/0267386 | A1 | * | 12/2005 | Copelan | 601/14 |

\* cited by examiner

*Primary Examiner* — Justine Yu
*Assistant Examiner* — Colin W Stuart
(74) *Attorney, Agent, or Firm* — Law Offices of Steven W. Weinrieb

(57) ABSTRACT

The present invention is a vacuum chamber tissue expander with a flexible sliding interface, which is applied externally over a specific region of tissue to apply a vacuum thereto so that the skin or other organ tissue can be expanded for treatments such as the subcutaneous grafting of fat cells. The flexible sliding interface accommodates and seals against flat or irregular tissue and slides along a mating groove in the vacuum chamber to provide an adjustable seal.

12 Claims, 9 Drawing Sheets

FLEXIBLE INTERFACE EXTERNAL MICRO VACUUM CHAMBER TISSUE EXPANDER

CROSS REFERENCES TO RELATED APPLICATIONS

None.

BACKGROUND OF THE INVENTION

1. Field of the Invention

The present invention pertains to a medical device, and more particularly, is for a flexible interface external micro vacuum chamber tissue expander.

2. Description of the Prior Art

Prior art tissue expander devices utilized a vacuum chamber having one open side which was to be applied externally over and about a specific region of skin tissue having an abnormality, anomaly, irregularity, and the like, or even over a skin tissue void of such mentioned features in order to apply a vacuum thereto so that the skin tissue can be reformed for the purpose of treatment of various sorts. These prior art devices often incorporated a skin tissue contact edge which lies in a plane, i.e., these devices presented a non-flexible flat contact surface edge. These prior art devices were often usually applied to flat skin tissue but were not adept in maintaining suitable contact nor in maintaining a steady and sufficient vacuum when applied to slightly irregular surfaces. Clearly what is need is a tissue expander device which overcomes the disadvantages of the prior art devices and which will have capabilities for flexibly, sealingly and accommodatingly contacting and then applying a suitable vacuum over and about a planar or non-planar skin tissue surface. Such a tissue expander device is provided by the present invention, hereby referred to as a flexible interface external micro vacuum chamber tissue expander.

SUMMARY OF THE INVENTION

The general purpose of the present invention is to provide a flexible interface external micro vacuum chamber tissue expander.

According to one embodiment of the present invention, there is provided a flexible interface external micro vacuum chamber tissue expander including a one-piece vacuum chamber having a top wall, a plurality of side walls continuous with each other and with the top wall and extending downwardly from the top wall, a downwardly facing open cavity formed by the top wall and the plurality of side walls, a plurality of receptor groove segments forming a continuous downwardly open receptor groove extending along the lower edges of the plurality of side walls, and a vacuum passage fitting communicating with the inside of the vacuum chamber. Also included in the present invention is a one-piece open top and open bottom flexible sliding interface having a plurality of walls, each having a top edge and a bottom edge. The flexible sliding interface is slidingly accommodated by the receptor groove at the lower region of the vacuum chamber. The lower edge of the flexible sliding interface is incorporated to flexibly, accommodatingly and sealingly contact irregular and/or regular planar skin tissue or other organ tissue. Vacuum is applied to the combined and mutually engaged vacuum chamber and flexible sliding interface to apply a negative pressure to the interior of the external tissue expander, thereby imparting a negative pressure to the skin or organ tissue where the skin or organ tissue is expanded into the open interior of the external tissue expander. Subsequent to the skin or organ tissue expansion and removal of the external tissue expander, the expanded skin tissue can be treated in various fashions, for example, the external skin tissue can be grafted or injected with fat cells for the purpose of reconstructive or other surgery.

One significant aspect and feature of the present invention is a flexible interface external micro vacuum chamber tissue expander having an open bottom vacuum chamber.

Another significant aspect and feature of the present invention is a flexible interface external micro vacuum chamber tissue expander having an open bottom and open top flexible sliding interface.

Another significant aspect and feature of the present invention is a flexible interface external micro vacuum chamber tissue expander having a flexible sliding interface accommodated by a receptor groove in the lower edge of the vacuum chamber.

Another significant aspect and feature of the present invention is a flexible interface external micro vacuum chamber tissue expander having a flexible sliding interface which flexingly, accommodatingly and sealingly contacts irregular and/or regular skin or organ tissue.

Yet another significant aspect and feature of the present invention is a flexible interface external micro vacuum chamber tissue expander which applies a negative pressure or vacuum to the interior of the vacuum chamber to promote expansion of the skin tissue and closely associated biological material into the interior cavity of the external tissue expander.

Still another significant aspect and feature of the present invention is to alter affected biological structures in preparations for other medical interventions and is designed to elevate and stretch, as well as to expand, reshape and reform tissues such as, but not limited to, skin, that are scarred from trauma, disease or developmental deformities.

Yet another significant aspect and feature of the present invention is to provide a method to expand, reshape and reform the epidermis, subcutaneous fat and connective tissue layer, and the muscle tissue.

Yet another significant aspect and feature of the present invention is to provide a method to alter affected biological structures in preparations for other medical interventions including, but not limited to, subcutaneous injection of biological materials whether manmade or natural.

Having thus briefly described one or more embodiments of the present invention, and having mentioned some significant aspects and features of the present invention, it is the principal object of the present invention to provide a flexible interface external micro vacuum chamber tissue expander

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
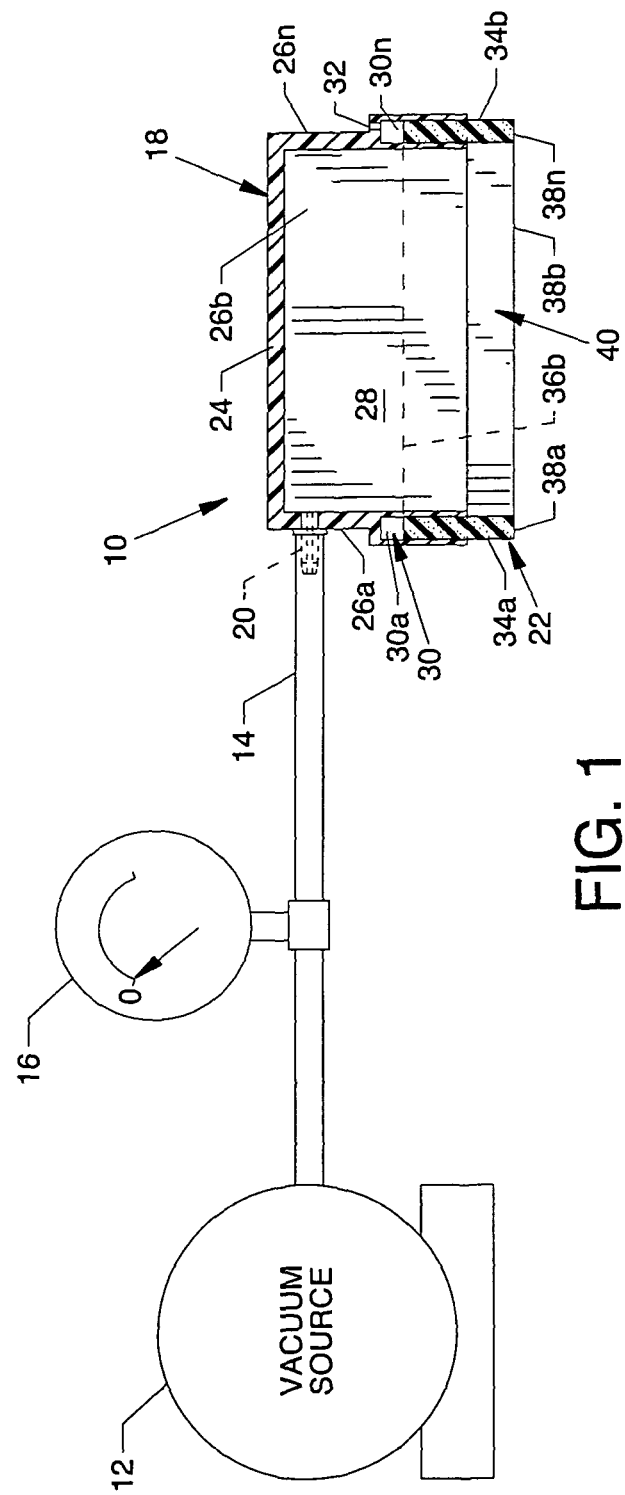
FIG. 1 is a side view in partial cross section showing a flexible interface external micro vacuum chamber tissue expander, the present invention, connected to and in use with a vacuum source, a vacuum delivery tube, and a vacuum gauge.

FIG. 1 is a side view in partial cross section showing a flexible interface external micro vacuum chamber tissue expander, the present invention, referred to herein as the tissue expander 10, connected to and in use with a vacuum source 12, a vacuum delivery tube 14 and a vacuum gauge 16. The tissue expander 10 is comprised generally of a one-piece open bottom vacuum chamber 18, a vacuum passage fitting 20, and a flexible sliding interface 22, each component of which is shown and described later in detail in FIG. 2 and other following illustrations that follow.

Figure 2:
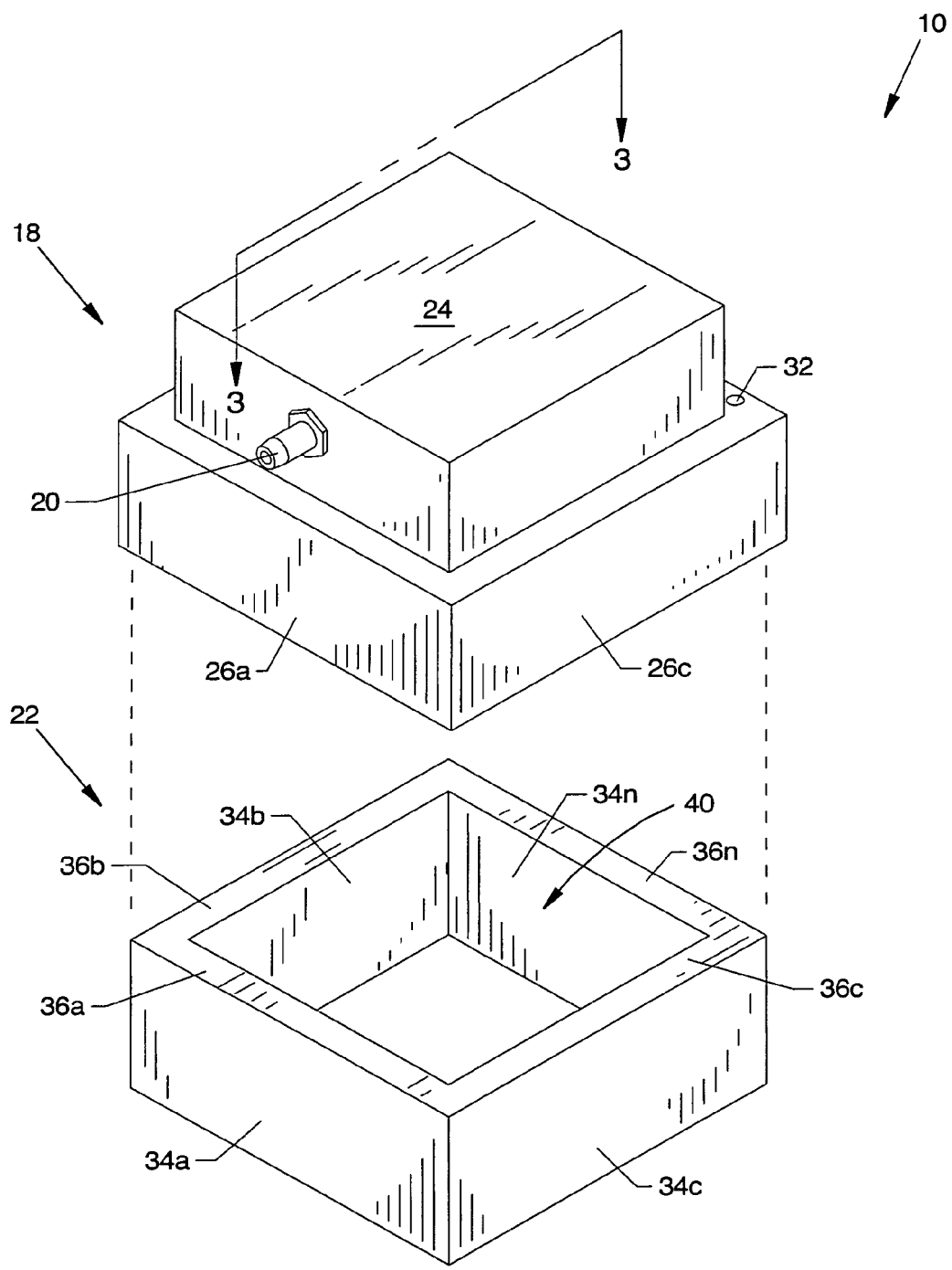
FIG. 2 is an exploded isometric view generally showing the flexible interface external micro vacuum chamber tissue expander including the one-piece open bottom vacuum chamber, the vacuum passage fitting and the flexible sliding interface.

FIG. 2 is an exploded isometric view generally showing the tissue expander 10, including the one-piece open bottom vacuum chamber 18, the vacuum passage fitting 20, and the flexible sliding interface 22.

Figure 3:
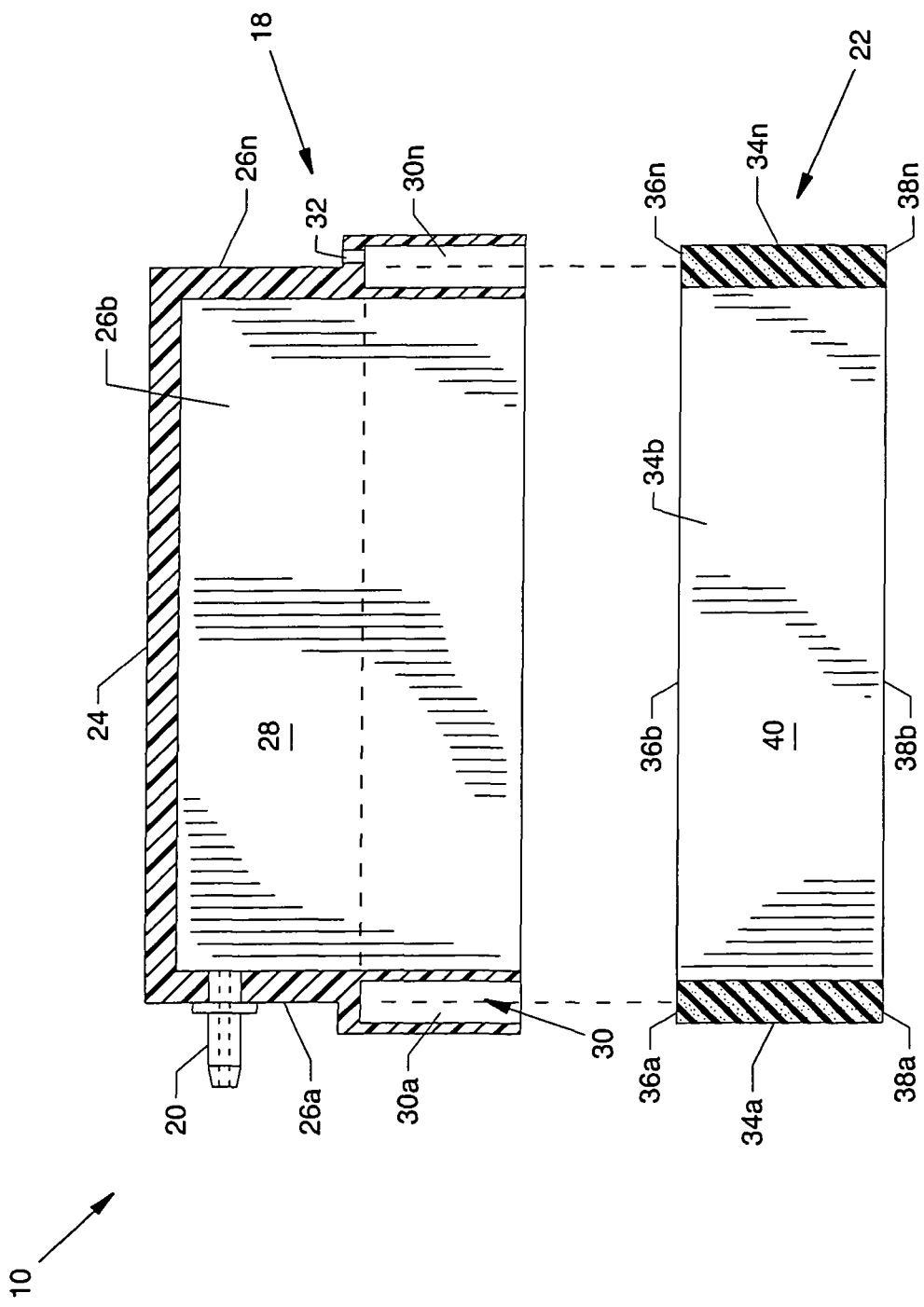
FIG. 3 is an exploded side view in cross section along line 3-3 of FIG. 2.

FIG. 3 is an exploded side view in cross section along line 3-3 of FIG. 2. With reference to the preceding figures and with reference to FIG. 3, the present invention is further described. The vacuum chamber 18, which can be of plastic or other suitable material, includes a top wall 24, a plurality of geometrically configured side walls 26a-26n continuous with each other and continuous with the top wall 24 and extending downwardly from the top wall 24, and an open cavity 28 formed by the inner surfaces of the top wall 24 and the inner surfaces of the plurality of the geometrically configured side walls 26a-26n. The lower regions of the geometrically configured side walls 26a-26n are expanded and of an increased thickness with respect to the upper regions of the geometrically configured side walls 26a-26n and include a plurality of receptor groove segments 30a-30n which form a continuous downwardly open receptor groove 30 extending within and along the lower regions of the plurality of the geometrically configured side walls 26a-26n. The vacuum passage fitting 20 communicates with the cavity 28 of the vacuum chamber 18 in order to impart a negative pressure, i.e., a vacuum, to the interior of the cavity 28. A pressure relief port 32 is also provided at the top of the receptor groove 30. The one-piece open top and open bottom flexible sliding interface 22, which can be of a durometer silicone or other suitable material, includes a plurality of continuously constructed walls 34a-34n continuous with each other having closely associated and corresponding top edges 36a-36n and bottom edges 38a-38n, respectively. Although the top edges 36a-36n and bottom edges 38a-38n, respectively, are shown in planar fashion, such edges, especially the bottom edges 38a-38n, could be of other suitable shapes, such as, but not limited to, semi-circular, semi-oval, one or more grooves, or other suitable configurations, and shall not be limiting to the scope of the invention. The inner surfaces of the walls 34a-34n delineate an open top and an open bottom cavity 40, such cavity extending therebetween. Additionally, the overall structures of the invention are shown having a square profile, but such structures can be of other geometric shapes and styles consistent with the principles of the invention, such as round, ovoid or other irregular or regular shaped profiles, and shall not be limiting to the scope of the invention.

Figure 4:
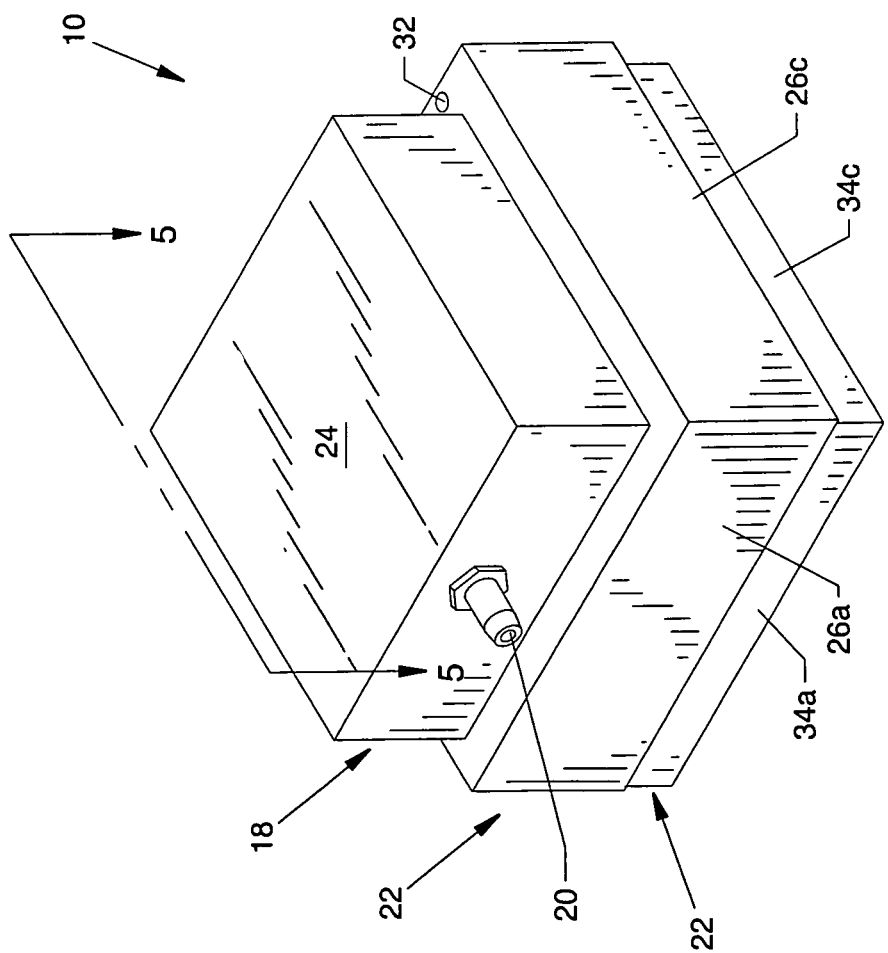
FIG. 4 is an isometric view generally showing the flexible interface external micro vacuum chamber tissue expander including the one-piece open bottom vacuum chamber, the vacuum passage fitting and the flexible sliding interface, and the vacuum passage fitting in engagement with the vacuum chamber.

FIG. 4 is an isometric view generally showing the tissue expander 10, including the one-piece open bottom vacuum chamber 18, the vacuum passage fitting 20 and the flexible sliding interface 22 in engagement with the vacuum chamber 18.

Figure 5:
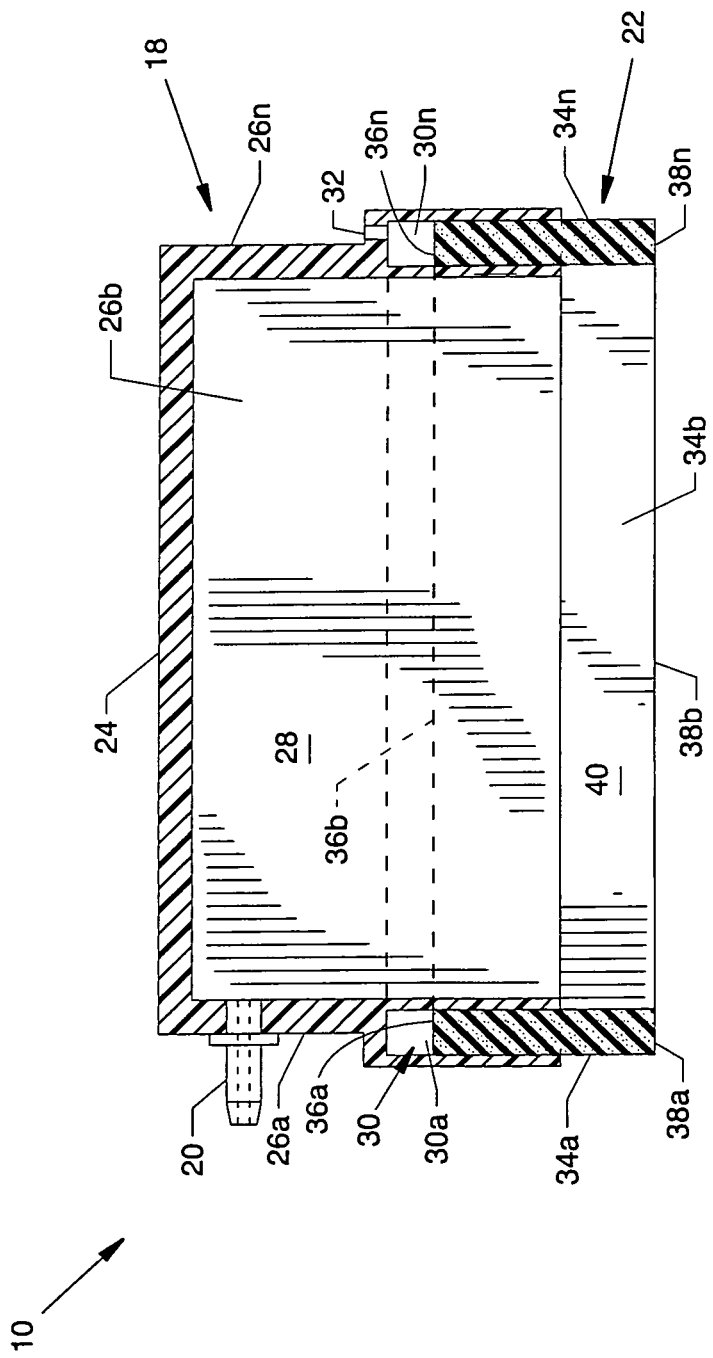
FIG. 5 is a side view in cross section along line 5-5 of FIG. 4 showing the mating of the flexible sliding interface to the vacuum chamber.

FIG. 5 is a side view in cross section along line 5-5 of FIG. 4 showing the mating of the flexible sliding interface 22 to the vacuum chamber 18. In particular, the walls 34a and 34n of the flexible sliding interface 22 are shown in partial sliding engagement with the receptor groove segments 30a and 30n at the lower regions of the geometrically configured side walls 26a and 26n of the vacuum chamber 18. Similar engagement of the walls 34b and 34c in partial sliding engagement with the receptor groove segments 30b and 30c at the lower regions of the geometrically configured side walls 26b and 26c of the vacuum chamber 18 occurs in a like and similar manner, wherein the engagement of the top edges 36a-36n of the walls 34a-34n and the upper regions of the walls 34a-34n of the flexible sliding interface 22 is continuous within the receptor groove 30 which is formed by the receptor groove segments 30a-30n.

Figure 6:
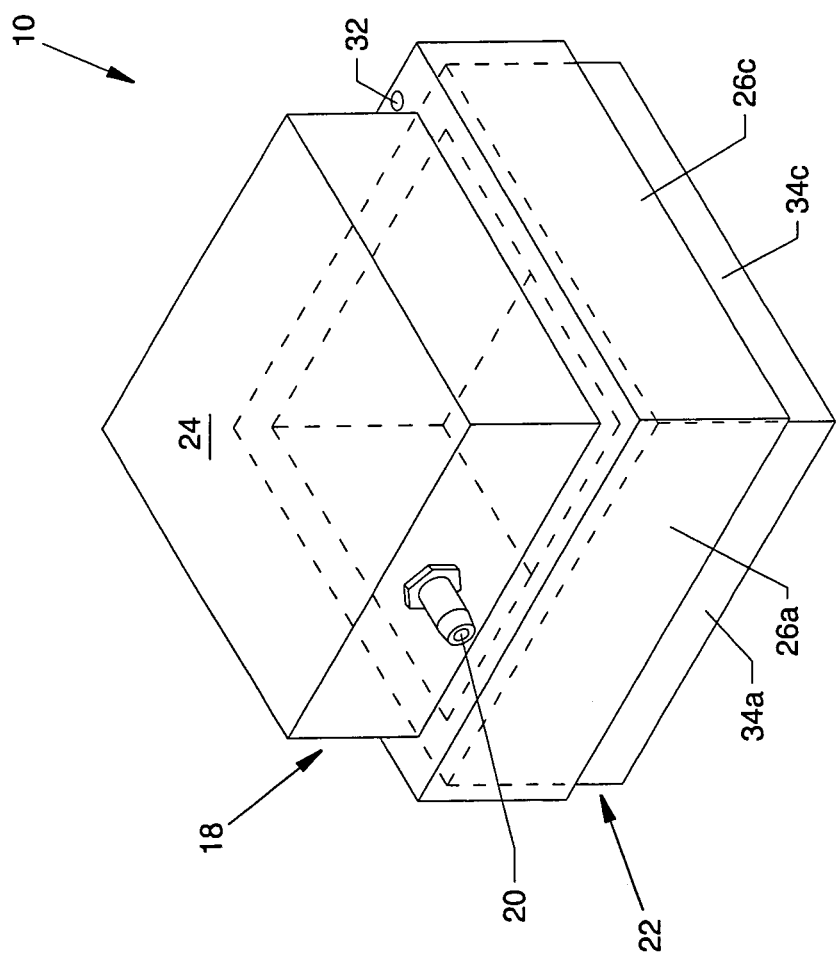
FIG. 6 is an isometric view generally showing the tissue expander including the one-piece open bottom vacuum chamber, the vacuum passage fitting and the flexible sliding interface, where the flexible sliding interface is shown in partial phantom lines in mutual engagement with the vacuum chamber.

FIG. 6 is an isometric view generally showing the tissue expander 10, including the one-piece open bottom vacuum chamber 18, the vacuum passage fitting 20, and the flexible sliding interface 22, where the flexible sliding interface 22 is shown in partial phantom lines in mutual engagement with the vacuum chamber 18.

MODE OF OPERATION

Figure 7:
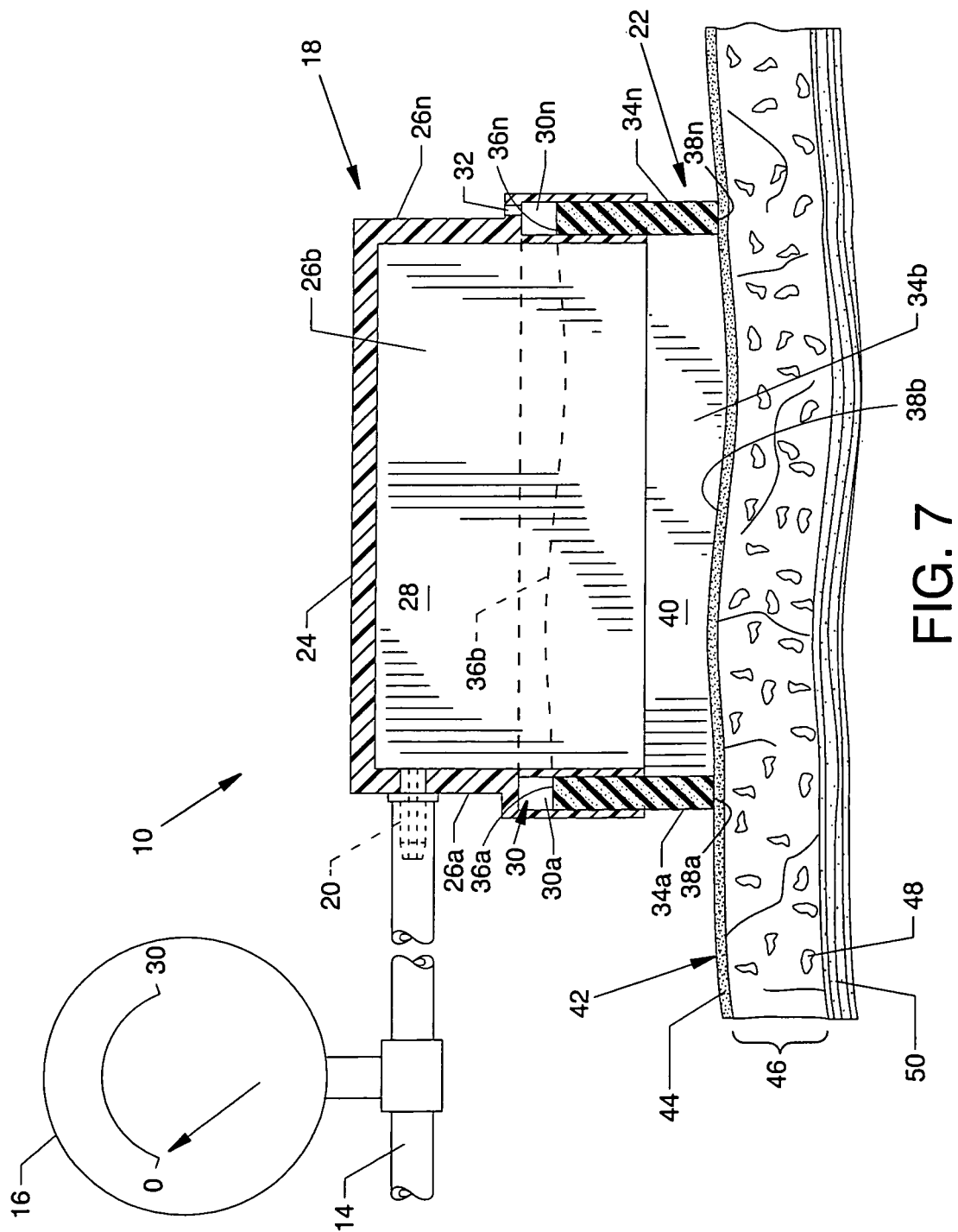
FIG. 7 is a side view in cross section like FIG. 5 showing the mated flexible sliding interface and vacuum chamber in flexible accommodating contact with tissue.

FIG. 7 is a side view in cross section similar to FIG. 5 showing the combined and mated vacuum chamber 18 and flexible sliding interface 22 in flexible and conforming contact with tissue having a surface that is irregular in contour and variable in texture or consistency. In this example, the tissue expander 10 is shown in close intimate contact with the surface of skin 42 having surface characteristics as just described. Layers depicted beneath and contained in the skin 42 include at least the epidermis 44, a subcutaneous fat and connective tissue layer 46, a plurality of fat cells 48 included in the subcutaneous fat and connective tissue layer 46, and muscle tissue 50 underlying the subcutaneous fat and connective tissue layer 46. Prior to application of vacuum to the combined vacuum chamber 18 and flexible sliding interface 22 as a unit, the bottom edges 38a-38n of the tissue expander 10 are brought into contact, whether urged by gravity or by applied force with the skin 42. The walls 34a-34n of the flexible sliding interface 22 flexibly and variably conform to the irregular shape (or planar shape) of the skin 42, where such vertical upwardly or downwardly flexing movement and geometric reshaping of the portion of the walls 34a-34n within the surrounding receptor groove segments 30a-30n is accommodated by space provided by the receptor groove segments 30a-30n comprising the receptor groove 30.

Figure 8:
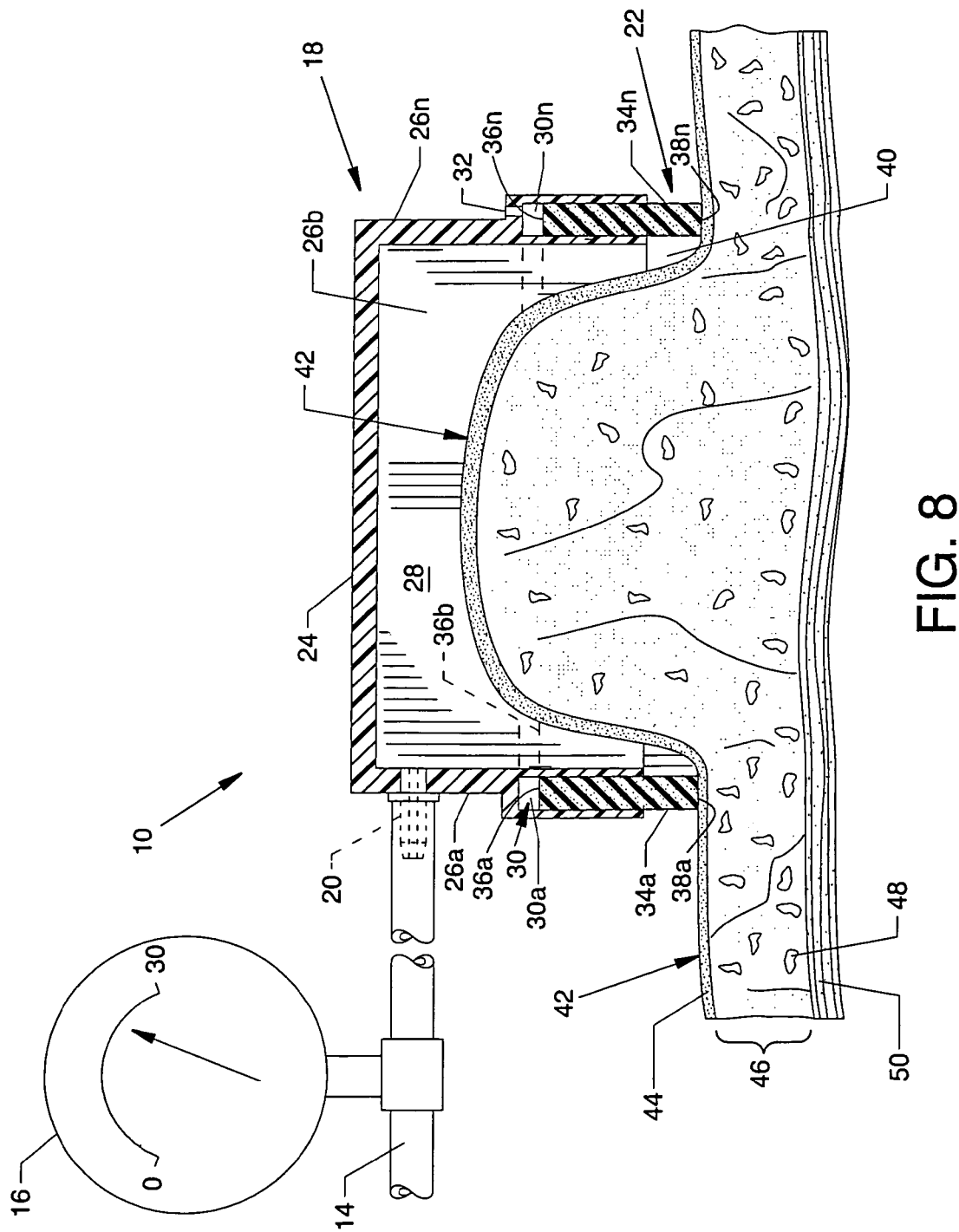
FIG. 8 is a side view in cross section like FIG. 7 showing the mated flexible sliding interface and vacuum chamber as a unit in flexible contact with skin having a surface that is irregular in contour and variable in texture or consistency where vacuum has been applied; and, FIG. 9 is a side view in cross section of the outwardly directed reformed and reshaped skin, where a lipo injection device is incorporated to inject grafted fat cells subcutaneously.
Figure 9:
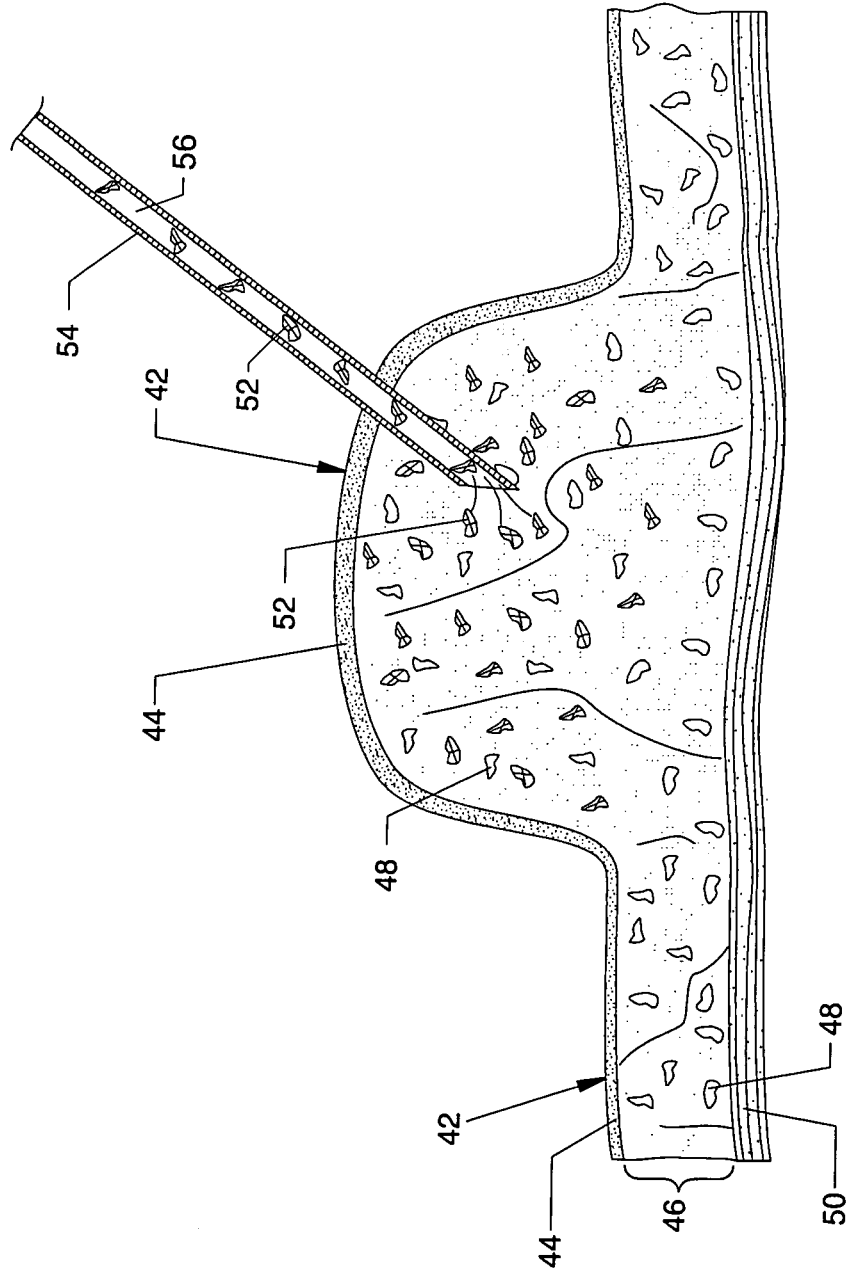

FIG. 8 is a side view in cross section similar to FIG. 7 showing the mated flexible sliding interface 22 and vacuum chamber 18 as a unit in flexible contact with skin 42 having a surface that is irregular in contour and variable in texture or consistency where vacuum has been applied by the vacuum source 12 through the vacuum delivery tube 14 and the vacuum passage fitting 20 to the combined cavities 28 and 40 of the vacuum chamber 18 and the flexible sliding interface 22, respectively, and to the skin 42. Such application of vacuum is preferably and controllably applied over time, the span of which can be of variable duration depending upon the desired degree of outwardly directed reformation and reshaping of the skin 42, including the epidermis 44, the subcutaneous fat and connective tissue layer 46, and the redistribution of the plurality of fat cells 48. Vacuum is applied in a range from one to twenty inches of negative pressure, accordingly. A pressure differential exists between the skin 42 and associated components and features thereof and the applied negative pressure (vacuum) at the combined cavities 28 and 40, whereby the relatively high pressure of the skin 42 and associated components and features assists in reforming, reshaping and urging of the skin 42 and associated components and features migratingly into the relatively low pressure region in the combined cavities 28 and 40. One desirable result is the expanding, reforming, reshaping and redistribution of the subcutaneous fat and connective tissue layer 46 whereby the spacing between the plurality of fat cells 48 is increased and the density of the connective tissue is decreased in order to accommodate grafted fat cells 52, as shown in FIG. 9. During such expanded deforming and urging of the skin, the contacted portion of the reforming skin 42 exerts an upward force against the bottom edges 38a-38n of the flexible sliding interface 22 to cause further accommodational sliding of the flexible sliding interface 22 into the receptor groove 30. The applied negative pressure sealingly draws the walls 34a-34n of the flexible sliding interface 22 inwardly and against the inwardly located outwardly facing surfaces of the receptor groove segments 30a-30n to effect a seal between the flexible sliding interface 22 and the side walls 26a-26n of the vacuum chamber 18, as well as enhancing the seal between the bottom edges 38a-38n with the skin 42 and drawing the tissue expander forcibly toward the skin 42.

FIG. 9 is a side view in cross section of the outwardly directed expanded, reformed and reshaped skin 42, comprised of the expanded reformed and reshaped epidermis 44, the expanded reformed and reshaped subcutaneous fat and the expanded reformed and reshaped connective tissue layer 46, including the expanded and redistributed plurality of fat cells 48. In this illustration, the tissue expander 10 has been removed from intimate vacuum influenced contact with the reformed and reshaped skin 42, including the expanded reformed and reshaped features and components described above. Such reforming and reshaping to expand the spacing between the plurality of fat cells 48 and the spacing and density of the connective tissue layer allows sufficient room for injection and accommodation of grafted fat cells 52 therein. In the alternative, insertion of biological materials, whether manmade or natural, can be inserted in close association with the superficial cutaneous structures. Such cutaneous injections can be accomplished by the use of a lipo injection device 54 having a lumen 56 to deliver a plurality of grafted fat cells 52 or other biological materials which stabilize and maintain the expanded reformed and reshaped geometry of the outwardly directed expanded reformed and reshaped skin 42.

Various modifications can be made to the present invention without departing from the apparent scope thereof

PARTS LIST 10 tissue expander
12 vacuum source
14 vacuum delivery tube
16 vacuum gauge
18 vacuum chamber
20 vacuum passage fitting
22 flexible sliding interface
24 top wall
26a-n side walls
28 cavity
30 receptor groove
30a-n receptor groove segments
32 pressure relief port
34a-n walls
36a-n top edges
38a-n bottom edges
40 cavity
42 skin
44 epidermis
46 subcutaneous fat and connective tissue layer
48 fat cells
50 muscle tissue
52 grafted fat cells
54 lipo injection device
56 lumen It is claimed:
1. A flexible interface vacuum chamber tissue expander comprising:
a one-piece vacuum chamber having a top wall, a plurality of side walls continuous with each other, each side wall having a lower edge and extending downwardly from the top wall so as to form with said top wall a first box structure having an open bottom defining with said top wall a downwardly facing open cavity internally within said one-piece vacuum chamber;
a plurality of receptor groove segments defined within each one of said side walls of said one-piece vacuum chamber and forming a continuous downwardly open receptor groove extending along the lower edges of the plurality of side walls, around said downwardly open box structure, and having top portions for respectively closing off said receptor groove segments;
a one-piece open top and open bottom flexible sliding interface having wall portions, defining a second box structure, respectively engaged within the receptor groove segments defining said continuous downwardly open receptor groove of the one-piece vacuum chamber and delineating an interface cavity in communication with the downwardly facing open cavity defined internally within the vacuum chamber for movement upwardly within said continuous downwardly open receptor groove of the one-piece vacuum chamber when bottom edge portions of said wall portions of said sliding interface are disposed in contact with tissue to be expanded; and a vacuum passage fitting communicating with the downwardly facing open cavity defined internally within the vacuum chamber so as to impart vacuum conditions to said downwardly facing open cavity defined within said vacuum chamber and to said interface cavity defined within said sliding interface when said wall portions of said sliding interface are disposed within said continuous receptor groove of said vacuum chamber.

2. The flexible interface vacuum chamber tissue expander of claim 1, wherein the vacuum chamber is formed of plastic.

3. The flexible interface vacuum chamber tissue expander of claim 1, wherein the flexible sliding interface is formed of silicone.

4. The flexible interface vacuum chamber tissue expander of claim 1, further comprising:
a pressure relief port in a top of the receptor groove.

5. The flexible interface vacuum chamber tissue expander of claim 1, wherein the interface cavity defines a shape selected from the group of shapes consisting of square, round, ovoid, and irregular.

6. The flexible interface vacuum chamber tissue expander of claim 1, further comprising a vacuum delivery tube and a vacuum source, said vacuum delivery tube being connected between said vacuum passage fitting and said vacuum source.

7. The flexible interface vacuum chamber tissue expander of claim 6, wherein said vacuum delivery tube has a vacuum gauge connected thereto.

8. The flexible interface vacuum chamber tissue expander of claim 1, wherein said continuous receptor groove in said side walls of said vacuum chamber has a closed upper end and a bottom open end with a pressure relief port in said closed upper end.

9. The flexible interface vacuum chamber tissue expander of claim 1, wherein each of the wall portions of said flexible sliding interface has a bottom edge and an upper portion, and wherein said bottom edge is selected from the group comprising planar, semi-circular, and semi-oval configurations.

10. The flexible interface vacuum chamber tissue expander of claim 1, wherein a bottom portion of each one of said plurality of side walls of said vacuum chamber is thicker than an upper portion of each one of said plurality of side walls of said vacuum chamber so as to define said plurality of receptor groove segments.

11. The flexible interface vacuum chamber tissue expander of claim 10, wherein said continuous receptor groove is defined within said thicker bottom portion of each one of said plurality of side walls of said vacuum chamber.

12. The flexible interface vacuum chamber tissue expander of claim 1, wherein said side walls of said vacuum chamber and said wall portions of said flexible sliding interface form a profile which is selected from the groups comprising a square profile, a rectangular profile, an ovoid profile, or other regular or irregular shaped profile.

\* \* \* \* \*